United States Patent [19]

Wiersema et al.

[11] Patent Number: 5,545,667
[45] Date of Patent: Aug. 13, 1996

[54] METHODS FOR TREATING NEOPLASMS WITH BETAINES

[75] Inventors: Richard J. Wiersema, Tracy; Jurij J. Hostynek, Lafayette, both of Calif.

[73] Assignee: The Clorox Company, Oakland, Calif.

[21] Appl. No.: 228,912

[22] Filed: Apr. 18, 1994

Related U.S. Application Data

[63] Continuation of Ser. No. 692,146, Apr. 26, 1991, abandoned.

[51] Int. Cl.$^6$ .................................................. A61K 31/205
[52] U.S. Cl. ........................................................ 514/556
[58] Field of Search ................................................ 514/556

[56] References Cited

FOREIGN PATENT DOCUMENTS

0004686A2  10/1979  European Pat. Off. ............... 514/556

OTHER PUBLICATIONS

Peterson et al. (1992) J. Med. Chem. 35:3991–4000.
Ashman et al. (1985) Mol. Immunol., 22:609.
Ashman et al. (1986) Immunol. Today, 7:28.
Coy et al. (1987) Federation Proceedings, 46(3):540, Abstr. 1303.
Ernst et al. (1980) Toxicology, 15:233.
Farber et al. (1958) Cancer Res., 18:1209.
Chemical Abstracts 114:135555C (1991) Abstracting Coy et al., Int. J. Immunopharmacol, 1990, 12(8), 871–81 (Eng)—Chemical Abstract Formula Index Part 2 & Part 3 pp. 219 0 F , 3348 F and 3349 F.

*Primary Examiner*—Jerome D. Goldberg
*Attorney, Agent, or Firm*—Townsend and Townsend and Crew

[57] ABSTRACT

The present invention provides a new therapeutic use of the zwitterionic surfactants, specifically betaines and sulfobetaines, to treat cellular, neoplastic disorders.

22 Claims, 3 Drawing Sheets

FIG. 1A

Growth inhibition in HL60 cells by $C_{12}$betaine, $C_{16}$betaine and $C_{16}$propylsulfobetaine

- $C_{12}$betaine
- $C_{16}$betaine
- $C_{16}$propylsulfobetaine

FIG. 1B

Growth inhibition in HL60 cells by $C_{12}$pentylbetaine and $C_{16}$pentylbetaine

- $C_{12}$pentylbetaine
- $C_{16}$pentylbetaine

Effect of $C_{16}$pentylbetaine on tritiated uridine, thymidine, and leucine uptake into HeLa cells

METHODS FOR TREATING NEOPLASMS WITH BETAINES

This is a continuation of application Ser. No. 07/692,146, filed Apr. 26, 1991, now abandoned.

TECHNICAL FIELD OF THE INVENTION

This invention relates generally to quaternary ammonium betaines and their selective use in the treatment of neoplasms.

BACKGROUND OF THE INVENTION

Previous investigations suggest that a class of compounds called "amphiphiles" have immunosuppressive activity and may inhibit cytotoxic T cell (Tc-cell)-mediated lysis of certain targets by Tc-cells generated in the mixed lymphocyte reaction (MLR) and thus may find utility as immunosuppressive agents. Amphiphiles have a hydrophobic tail attached to a hydrophilic head group. The tail, generally of hydrocarbons, may consist of one or two chains, and the head group may bear a positive or negative charge, or may be uncharged. Because most biological membranes carry a net negative charge, the compounds used in the study by Ashman, et al [(1985) *Mol Immunol* 22:609 and (1986) *Immunol Today* 7:278] primarily involved cationic mono- and di-alkyl quaternary ammonium compounds. In particular, PCT publication WO85/05031 discloses a double-chained quaternary ammonium surfactant, didodecyl dimethyl ammonium bromide, when used at dosages between 10 ng/ml and 100 ug/ml, was immunosuppressive on alloreactive Tc cells.

A study of the alleged immunosuppressive activity reported in the above literature was initiated, given the use of these compounds in commercial formulations of hair care products, nonirritant shampoos, liquid soaps and gels, disinfectants, laundry additives and, together with heterocyclic quaternaries, as particularly effective fabric softeners (Linfield (1970) In: *Cationic Surfactants* (ed. Jungermann, E.) pp. 48–52, Marcel Dekker, Inc., New York). The results of this study are summarized in Coy, et al. (1987) *Federation Proceedings* 46(3):540, Abstract No. 1303. This publication provides the concentration ranges in which five amphiphilic compounds exhibited immunosuppressive and/or cytotoxic activity in the one-way mixed leukocyte reaction (MLR). The authors conclude that there may be a critical concentration range in which immunosuppression is achieved without cytotoxicity. Exposure of the promyelocytic cell line HL-60 to these amphiphiles caused dose-dependent inhibition of proliferation but it also significantly reduced cell viability. However, at concentrations that did not alter viability, no inhibition of proliferation was seen. Neither betaines or sulfobetaines were included in this study.

A more exhaustive study with 29 amphiphiles was prepared and reported at the Biomedical Research Committee of the Soap and Detergent Association, held 21 Jul. 1988 in New York, N.Y. In the MLR, seventeen of twenty-nine compounds investigated produced greater than 70% inhibition without toxicity and six compounds were toxic (i.e., end viability and live cell percentage were less than 50% of the control). In order to determine whether the inhibitory capabilities of the amphiphiles were specific for lymphocyte proliferation or whether the amphiphiles would inhibit proliferation of other cells, fourteen compounds, including two betaines, were tested on a battery of cell lines. The only betaines tested were N-(carboxymethyl)-N,N-dimethyl-1-dodecanaminium hydroxide (HB-1) and N-dodecyl-N,N-dimethyl-1-ammonio-1-propanesulfonate (HSB-3).

The results showed that the effect of these compounds was antiproliferative (lack of cell growth, but viable cells) rather than immunosuppressive (cellular failure to respond to extracellular chemical stimulus). At the concentrations tested HB-1 was found to be inhibitory and toxic and HSB-3 was found to be noninhibitory and nontoxic.

Ernst and Arditti, (1980) *Toxicology* 15:233–242 tested thirteen nonionic surfactants for toxic effects to HeLa cells. The surfactants consisted of fatty alcohol ethoxylates and 6 amphoterics (all 3-(alkyldimethylammonio)-1-propanesulfonates having an alkyl chain from 8 to 18 carbon atoms. Lethal concentrations ranged from 16 to 320 mM. Ernst et al., did not test these compounds for their ability to inhibit growth of HeLa cells.

Farber and Ichinose, (1958) Cancer Res 18:1209 report that betaine was relatively effective in preventing chronic morphological changes in the liver, including cancer formation, induced in rats fed ethionine. Possible mechanisms for its effectiveness were presented, including its possible role as a substitute for methyl transferase in the conversion of homocysteine to methionine. It is known that methionine is capable of inhibiting many effects of ethionine administration.

A principal object of this invention is to provide quaternary ammonium compounds which are biologically active antineoplastic agents.

SUMMARY OF THE INVENTION

The invention provides pharmaceutical compositions comprising quaternary ammonium betaine compounds which are useful for inhibiting cellular growth associated with neoplastic disorders.

More particularly, the quaternary ammonium betaine compounds used in the above compositions comprise the formula:

wherein $R_1$ is independently selected from the group consisting of lower alkyls and alkylaryls;

X is selected from the group consisting of carboxyl anions, phosphonate anions, and sulfonate anions;

m is an integer from 9 to 15; and n is an integer from 1 to 5; provided the combination of X, m, and n result in compounds having a Krafft point at or below 25° C. and a critical micelle concentration about or less than 50 uM.

As represented by the above formula, amphiphiles of the present invention are zwitterionic surfactants and are, more particularly, betaines and sulfobetaines (alkyldimethyl-ammonio carboxylates and sulfonates). Betaines and sulfobetaines are used primarily as specialty surfactants in personal care products. They are not irritating to the skin or eyes, and are compatible in mixtures with either anionic or cationic surfactants. They have been found to be useful in foam production and stabilization, and in hair conditioning. Other attributes include detergency, emulsification, viscosity building, wettability and dispersibility. Surprisingly, it has been found that this class of compounds are strong inhibitors of tumorous cell lines, indicating their use as effective antineoplastic agents.

MODES OF CARRYING OUT THE INVENTION

A. The Compounds Useful in the Invention

In this specification and in the claims which follow it reference will be made to a number of terms which shall be defined to have the following meanings.

"Critical micelle concentration" or "cmc" refers to the point at which micelle formation begins.

"Kraft point" refers to the temperature at which the solubility of the surfactant equals the cmc.

"Lower alkyl" means a branched or linear, saturated or unsaturated hydrocarbon group of one to four carbon atoms such as, methyl, ethyl, i-propyl and n-butyl and the like. For use herein, methyl and ethyl are preferred lower alkyls with methyl in general being the more preferred.

"Lower alkylaryls" means a branched or linear, saturated or unsaturated hydrocarbon group of one to four carbon atoms such as, methyl, ethyl, i-propyl and n-butyl and the like attached to aryl.

"Quaternary ammonium betaine" means a quaternary ammonium dipolar surfactant in which the charged ions are nonadjacent. This definition includes quaternary ammonium derivatives such as, for example, sulfobetaines, amidobetaines, and mono- and dialkyl betaines.

Surfactant nomenclature uses a shorthand notation, e.g., 12-1B, wherein the first number (12) is the alkyl chain length, the second number (1) is the tether length (carbon chain length between the nitrogen and the anionic group), and the B, S or P designates a carboxylic acid, sulfonate or phosphonate terminus, respectively.

Synthetic methods are available for the chemical synthesis of betaines (for a review of the preparative methods, analytical methods and physical properties of betaines see Ernst and Miller in "Amphoteric Surfactants"; Bluestein et al., Eds.; *Surfactant Science Series*, Marcel Dekker, Inc., New York (1982) Vol. 12, Chapter 2, which is incorporated herein by reference). A simple and general two-step procedure based on these synthetic methods is reported in Crichlow et al., [(1989) *Acc Pio Res* 2(1):2–47, which is incorporated herein by reference]. Briefly, the two-step procedure for the synthesis of betaines with various tether lengths is outlined below.

This synthetic procedure may be used for the preparation of betaines containing one, three, four, five or six methylene units separating the cationic and anion charges. In first step of this method a tertiary amine and an alkyl chloride or alkyl bromide monoester are combined to form the corresponding quaternary ammonium salt. This reaction may be performed in a variety of organic solvents including: ethyl, acetate, ethanol, isopropanol or in the absence of a solvent. The resulting crude ammonium salt is then dissolved in isopropanol or methanol and treated with the anion exchange resin AG1-X8 (hydroxide form). The hydroxide ion that is associated with the cationic resin effects an ester hydrolysis of the ethyl or methyl ester which results in the liberation of the betaine. Once formed, the betaine is isolated and purified in fair to good overall yields by recrystallization. Following this procedure the use of labor intensive large scale liquid chromatography may be avoided.

The synthesis of betaine 12-2B cannot be prepared by the above procedure. For example, treatment of ethyl 3-bromopropionate with N,N-dimethyldodecylamine results in the formation of ethyl acrylate and the hydrobromide salt of the tertiary amine. This observation is not unexpected and presumably occurs from the base promoted dehydrobromination of 3-bromopropionate by N,N-dimethyldodecylamine to give the thermodynamically favored ethyl acrylate. An alternative method for the synthesis of the 12-2B betaine is illustrated below. Treatment of β-propiolactone with N,N-dimethyldodecylamine results in the direct formation of betaine 12-2B. This reaction may be envisaged to proceed by nucleophilic ring opening of the strained lactone ring at the C-3 position by the tertiary amine. Isolation and purification of the product by flash chromatography gives the betaine 12-2B in isolated yield.

Sulfobetaines containing three and four methylene groups between the sulfur and nitrogen atoms can be prepared by treatment of the tertiary amines with the corresponding commercially available sultones (1,3-propane sultone and 1,4-butane sultone, respectively). For example, the 16-4S sulfobetaine may be synthesized as shown below:

Additional sulfobetaines useful in the present invention may be prepared via a two-step procedure that begins by a reaction between the t-amine and a large excess (to ensure reaction at one end of the molecule only) of an alpha-omega dibromide to form a bromo-quaternary bromide salt. The latter is treated with aqueous bisulfite resulting in formation of the desired sulfobetaine compound. By the proper choice of starting dibromide, the desired number of carbon atoms can be inserted between the sulfur and nitrogen atoms thus making this a very general procedure. For example, the method used to prepare the sulfobetaine 16-2S is shown below:

Preferred embodiments of the quaternary ammonium betaines provided herein for use in the methods of the invention are:

| Name/Structure | Molecular Weight | Abbrev. |
|---|---|---|
| N-(carboxymethyl)-N,N-dimethyl-1-dodecanaminium hydroxide inner salt $C_{12}H_{25}N^+(CH_3)_2$—$CH_2$—$CO_2^-$ | 271.5 | (12-1B) |
| N-(carboxymethyl)-N,N-dimethyl-1-hexadecanaminium hydroxide inner salt $C_{16}H_{33}N^+(CH_3)_2$—$CH_2$—$CO_2^-$ | 328.0 | (16-1B) |
| N-hexadecyl-N,N-dimethyl-3-ammonio-1-propanesulfonate $C_{16}H_{33}N^+(CH_3)_2$—$(CH_2)_3$—$SO_3^-$ | 392.0 | (16-3S) |
| N-dodecyl-N,N-dimethyl-3-ammonio-1-propanesulfonate $C_{12}H_{25}N^+(CH_3)_2$—$(CH_2)_3$—$SO_3^-$ | 335.6 | (12-3S) |
| N-5-(carboxypentyl)-N,N-dimethyl-1-hexadecanaminium hydroxide inner salt $C_{16}H_{33}N^+(CH_3)_2$—$(CH_2)_5$—$CO_2^-$ | 383.7 | (16-5B) |

B. Antineoplastic Activity

The usefulness of the invention compositions is demonstrated by testing the compounds in a number of tumor cell lines. Established cell lines are the system of choice for the prescreening of unknown compounds for antineoplastic activity. The tumor cell line screen works on the following principle. Cancer cells, if provided with enough nutrients, will grow unchecked in vitro, allowing researchers to grow many types of cancer cells outside the body. To perform an assay, standard amounts of the various cancer cells are placed in individual wells of a microtiter plate, and incubated with the potential antineoplastic compound of interest, for a sufficient period of time to allow for at least a 6-fold control growth, generally 1 to 5 days depending on cell origin. At the end of the incubation period, the cell lines are stained and assayed by a variety of means including, for example, proteins stains or a colorimeter for normal growth, growth inhibition or cytotoxicity. These assays measure a compound's ability to inhibit cell growth and a positive response of the compounds in these assays would be indicative of the therapeutic potential of these compounds. See, for example, the protocols and data presented in Laskin et al., (1979) Cancer Res 39:383–390 for 5-fluorouracil in mouse and human cells in culture. The measurement of growth inhibition appears superior to other means of measuring the effect of antineoplastic agents in that it more accurately reflects the antiproliferative effect.

The data provided herein show that the cellular inhibitory effects occur in the region of the critical micelle concentration (cmc) of the surfactant. Given the basic requirement of the zwitterionic nature of the compounds, the cmc is largely dominated by the alkyl, aryl or akylaryl chain length, with little effect by the tether length of the anionic terminus. Generally, the compounds useful in the present invention will exhibit a cmc of about or less than 50 uM.

A necessary corollary to the cmc concentration is that the Krafft points of the surfactants must be about or less than 25° C. (approximately room temperature). Krafft points are controlled by the tether length and the anionic end group; the longer the tether length the higher the Krafft point, and the sulfonate end group generally has a higher Krafft point than the carboxylic acid group.

The high degree of activity of the compounds of the invention coupled with their low relative toxicity makes them particularly desirable oncolytic agents for use in humans and suitable candidates for a clinical trial. Such clinical trials are generally carried out in accordance with a procedure by Carter in "Study Design Principles for the Clinical Evaluation of New Drugs as Developed by the Chemotherapy Programme of the National Cancer Institute"; *The Design of Clinical Trials in Cancer Therapy*, Staquet, Ed.; Futura Publishing Co., New York, (1973) pp.242–289. This article refers to standard "signal" cell lines which have been designated by the National Cancer Institute as those tumors against which clinical trial candidates should be screened. These include leukemia, small cell and non-small cell lung cancer, colorectal cancer, melanoma, brain cancer, renal cancer, and ovarian cancer. The compounds of the invention would be tested clinically by the oral or parenteral route against these tumors as well as other tumors known to be susceptible to i.v. administration of proven oncolytic agents, such as, for example, 5-fluorouracil and methotrexate. After its potency, and the nature and degree of side effects had been established, the drug would be tried against tumors for which there is no therapy. After preliminary tests were concluded and the results analyzed, the drug would be used against tumors susceptible to its action at relatively non-toxic dose levels.

C. Formulation and Administration

Administration of the active compounds described herein can be via any of the accepted modes of administration for therapeutic agents. These methods include parenteral (intravenously, subcutaneously, intramuscularly, intraspinally, intraperitoneally, and the like), oral, transdermal and other system modes.

Depending on the intended mode, compositions containing a compound of the invention may be in liquid dosage forms, such as liquids or solutions, preferably in unit dosage forms suitable for single administration of precise dosages. The compound, depending on the form and concentration used, can be either suspended or dissolved in the vehicle. In preparing solutions, a water-soluble form of the compound can be dissolved in water for injection and filter sterilized before filling into a suitable vial or ampule and sealing. The compositions will include a conventional pharmaceutical vehicle and an active compound of the invention and, in addition, may include other adjuvants, antioxidants, preservatives and buffering agents.

Such pharmaceutically acceptable vehicles are typically nontoxic and nontherapeutic. Examples of such vehicles are water, aqueous vehicles such as saline, Ringer's solution, dextrose solution, and Hank's solution and nonaqueous vehicles such as fixed oils (e.g., corn, cottonseed, peanut, and sesame), ethyl oleate, and isopropyl myristate. Sterile saline is a preferred vehicle and the compounds are sufficiently water soluble to provide a solution for all foreseeable needs. Actual methods of preparing such dosage forms are known, or will be apparent to those skilled in this art; for example, see *Remington's Pharmaceutical Sciences,* Mack Publishing Company, Easton, Pa., 15th Edition, 1975. The composition or formulation to be administered will, in any event, contain a quantity of the active compound(s), a therapeutically effective amount, i.e., in an amount effective to achieve the desired therapeutic response in the subject being treated.

To enhance the stability, the composition can be frozen after filling into the vial and the water removed under vacuum. The dry lyophilized powder in then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by sterilization. Advantageously, a wetting agent is included in the composition to facilitate uniform distribution.

The amount of the compositions administered to the subject is sufficient to cause regression of the target tumor cells but below that which may cause severe toxicity. This amount will depend upon the nature of the disease state, the antitumor spectrum of the specific betaine compound of the invention, the species of the subject being treated, the indication dosage intended and the weight or body surface of the subject. With parenteral administration, the intravenous route is preferred although, with smaller mammals such as mice, the intraperitoneal route may be used. For intravenous administration, isotonic solutions containing 1–50 mg/ml of a salt of formula I are employed. The drug is administered at a dose of from 0.01 to 10 mg/kg and preferably from 0.05 to 1 mg/kg of mammalian body weight once or twice a week or every two weeks depending on both the activity and the toxicity of the drug.

A more recently revised approach for parenteral administration employs the implantation of a slow-release or sustained-release system, such that a constant level of dosage is maintained. See, for example, U.S. Pat. No. 3,710,795, which is incorporated herein by reference.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. The oral dosage is from 2 to 10 times the intravenous dose.

The following examples further illustrate the compositions used in the method of the invention, and are not intended to limit the invention in any manner.

EXAMPLES

Example 1

Synthesis of Betaines

For all compounds synthesized in this example, $^{13}$C NMR spectra were recorded on a Bruker MSL 400 at a frequency of 100.614 MHz in $CDCl_3$. The 77.0 ppm resonance of $CDCl_3$ from TMS was used as an internal reference for all $^{13}$C NMR spectra. Infrared spectra were recorded on a Perkin Elmer 283B Infrared Spectrophotometer. Mass Spectra were measured on a Finnigan MAT 212 mass spectrometer using the positive ion fast atom bombardment ionization mode with Xenon gas. Melting points were determined using a Electrothermal melting point apparatus and are uncorrected. All reaction solvents and chromatography solvents were purchased from either EM Science or J. T. Baker and were used without purification. N,N-dimethyldodecylamine (Aldrich Chemical Co.) and N,N-dimethylhexadecylamine (Armak Chemicals) were purified by distillation from sodium hydroxide. Methyl chloroacetate, β-propiolactone, ethyl 6-bromohexanoate, methyl 5-bromovalerate (Aldrich Chemical Co.) and ethyl 4-bromobutyrate (Fluka Chemical) were used without purification. The purity of the betaines was determined by titration of an acetic acid solution of the betaine with perchloric acid. Water concentrations were determined by Karl Fischer titration. Thin layer chromatography was performed on Analtech HPTLC-GHLF normal phase silica gel plates and Baker-flex aluminum oxide IB-F sheets. Column chromatography was performed on Sepralyte preparative grade 230–400 mesh silica gel. AG 1-X8 anion exchange resin, 20–50 mesh, hydroxide form was purchased from Bio-Rad Laboratories.

N-(3-carboxypropyl-N,N-dimethyl-1-dodecanaminium hydroxide inner salt, betaine 12-3B. A solution of 24.0 g (0.123 moles) of ethyl 4-bromobutyrate and 25.0 g (0.117 moles) of freshly distilled N,N-dimethlydodecylamine was delivered to a flame dried, 3-necked, 1000 mL round bottom flask fitted with a mechanical stirrer, gas inlet and glass stopper. The initially colorless solution was mechanically stirred at 60° C. for 21 hours under an atmosphere of argon. During this time, a viscous light gold oil was formed. The oil was diluted with 600 mL of 2-propanol and 150 g of AG 1-X8, 20–50 mesh, hydroxide form anion exchange resin was added. The resulting suspension was stirred for 17 hours at room temperature in the air. The suspension was filtered by gravity through a paper filter to remove the anion exchange resin and the filtrate was concentrated under reduced pressure (aspirator). The crude betaine 3–12 was dried under reduced pressure (0.5 torr) overnight. The dried white material was recystallized twice from ether/methanol and 22.00 g (0.074 moles, 63%) of pure betaine 3–12 was isolated as a white crystalline solid that contained 2% water: mp 138°–140° C. $^{13}$C NMR ($CDCl_3$): 13.62, 19.60, 22.13, 25.89, 28.71, 28.79, 28.94, 29.05, 31.36, 34.02, 50.51, 63.39, 63.88, 174.98 ppm.

N-(5-carboxypentyl)-N,N-dimethyl-1-dodecanaminium hydroxide inner salt, betaine 12-5B. A mixture of 43.5 g (0.204 moles) of ethyl 6-bromohexanoate and 43.5 g (0.204 moles) of N,N-dimethlydodecylamine at 65° C. for 18 hours produced a viscous oil that was diluted with 500 mL of 2-propanol and treated with 300 g of AG 1-X8. Isolation of the crude betaine 5–12 by flash column chromatography on silica gel using ethyl acetate/methanol (1/1–1000 mL) and methanol (1500 mL) followed by recrystallization from ether/methanol at −70° C. yielded 16.1 g (0.049 moles, 24%) of pure betaine 5–12 that contained 1.1% water: mp 201°–4° C. $^{13}$C NMR ($CDCl_3$): 13.57, 21.83, 22.12, 22.22, 25.60, 25.85, 26.05, 28.73, 28.91, 29.03, 31.34, 38.28, 50.32, 63.20, 177.49 ppm.

N-(carboxymethyl)-N,N-dimethyl-1-hexadecanaminium hydroxide inner salt, betaine 16-1B. A three-necked, 5-L round bottomed flask was equipped with a condenser, a heating mantle, and charged with 1.5 L of isopropanol, 290.77 g (1.08 mole) of dimethylcetylamine, and 262.4 g (2.42 mole) of methyl chloroacetate. The solution was refluxed overnight, the solvent evaporated at reduced pressure, and the oil vacuum dried. This produce (561.8 g) was recystallized from 830 mL of ethanol with cryokool cooling (−15° C.). The filtrate was repeatedly cooled and filtered and all the filtrants were collected by dissolving to give 212.6 g. More material (238.8 g) was obtained by triturating the evaporated mother liquor with acetone, collecting by suction filtration, and vacuum drying. A 4-L beaker was equipped with a mechanical stirrer and charged with 504 g of Bio-Rad AG 1-X8 resin (washed sequentially with MeOH, $H_2O$, MeOH). The above material (160 g, 0.42 mole) was added and the mixture was mechanically stirred overnight in 2-L of methanol. The mixture was suction filtered and evaporated at reduced pressure. The oil was azeotroped with benzene until a colorless benzene solution resulted. The solvent was then evaporated at reduced pressure and briefly vacuum dried to give 152.8 g of solid material. This was partially recrystallized from 150 mL of isopropanol. The semi-solid in the isopropanol was stirred at 7° C. and diluted with 200 mL of anhydrous ether. Product was then collected by a repeated cooling-filtration sequence, and dried overnight in vacuo (40° C.) over NaOH pellets. This was combined with another batch of material prepared in like manner and this combination was analyzed (43% yield overall). The sample contained 3.8% water:NMR ($CDCl_3$) 13.58, 22.20, 22.82, 26.23, 29.19, 31.76, 51.04, 64.12, 65.12, 165.14 ppm; IR ($CDCl_3$) 3600–3100(w), 3100–2800(s), 1650(s), 1100–1000(s)$cm^{-1}$.

N-(5-carboxypentyl)-N,N-dimethyl-1-hexadecanaminium hydroxide inner salt, betaine 16-5B. A mixture of 254.9 g (1.102 moles) of ethyl 6-bromohexanoate and 270.0 g (1.001 moles) of N,N-dimethylhexadecylamine at 60° C. for 18 hours produced a viscous oil that was diluted with 3500 mL of 2-propanol and treated with 500 g of AG 1-X8. The reaction suspension was stirred for 36 hours and then 300 mL of 2-propanol and 300 g of AG 1-X8 were added. Recrystallization of the crude betaine 5–16 twice from ether/methanol yielded 216.1 g (0.563 moles, 56%) of pure betaine 5–16 that contained 2.7% water: mp 119 (softens), 173°–175° C. (melts). $^{13}C$ NMR ($CDCl_3$): 14.13, 22.15, 22.53, 22.74, 25.72, 25.88, 26.04, 26.12, 29.32, 29.37, 29.54, 29.70, 30.01, 30.10, 30.18, 31.93, 50.93, 63.71, 63.80, 178.43 ppm.

N-hexadecyl-N,N-dimethyl-3-ammonio-1-propanesulfonate (16-3S sulfobetaine) available as zwittergent 3-08 detergent—item 693019; N-dodecyl-N,N-dimethyl-3-ammonio-1-propanesulfonate (12-3S sulfobetaine) available as zwittergent 3-12 detergent—item 693015; and N-octyl-N,N-dimethyl-3-ammonio-1-propanesulfonate (8-3S sulfobetaine) available as zwittergent 3-16 detergent—item 693023 were all commercially obtained from Calbiochem (San Diego, Calif.).

Example 2

Cell Growth Inhibition Assays

A total of ten cell lines were used to evaluate the growth inhibitory potency of the various surfactants. In these studies, human, rat, mouse and bovine cells were used. A spectrum of different tumor cell types were used including those derived from keratinocytes (PAM 212), leukemias (HL-60, U-937 and K-562), an epitheloid carcinoma (HeLa) and melanoma (B-16). The B16 melanoma was used since this is a common cell type used to evaluate antimetastatic activity of test compounds. The effect of the surfactants on three fibroblast cell lines (C3H 10T1/2, NIH 3T3 and R6) were also evaluated for comparison to the tumor cell lines. The activity of the surfactants was also evaluated using pulmonary aortic endothelial cells for effectiveness as anti-angiogenic agents.

PAM 212 cells are a mouse keratinocyte-derived tumor cell line. U-937 cells are a human histiocytic tumor cell line. HeLa cells are an epitheloid tumor cell line. Three murine fibroblast cells lines tested included the mouse fibroblast cell line, C3H 10T1/2, the rat fibroblast cell line R6, and the NIH 3T3 mouse fibroblast cell line. The human leukemia cell line HL-60 and the mouse melanoma B-16 cell were also tested. K-562 cells were from the American Type Culture Collection. All cells were grown in Dulbecco's modified Eagle's medium in a 37° C. incubator in an atmosphere of 5% $CO_2$.

For growth inhibition assays, cells were seeded at low density ($2.5 \times 10^4$ cells in 0.5 ml of culture medium) into 24-well tissue culture plates (Falcon Labware, Lincoln Park, N.J.). After 24 hours at 37° C., increasing concentrations (1 to 100 uM) of the surfactants were added to the cells in the culture plate. Control cultures were incubated in the absence of any surfactant. The cells were then incubated for 3–4 days to allow for growth. Cells from individual wells in the culture plate were then removed and duplicate samples taken for counting using a Coulter counter. To remove adherent cells the plates were treated with 0.25% trypsin/0.2% EDTA (GIBCO, Grand Island, N.Y.).

As shown in Table 1 below, each of the cell lines were found to be sensitive to at least three of the compounds. Data is presented as percentage of growth inhibition at each concentration tested when compared to the control untreated cultures.

TABLE 1

Effect of Surfactants on Cell Growth
$IC_{50}$
(uM CONC. INHIBITING GROWTH OF THE CELLS BY 50%)

| | (12-3S) $C_{12}$propyl-sulfobetaine | (8-3S) $C_8$propyl-sulfobetaine | (12-5B) $C_{12}$pentyl-betaine | (16-5B) $C_{16}$pentyl-betaine | (12-1B) $C_{12}$betaine | (16-1B) $C_{16}$betaine | (16-3S) $C_{16}$propyl sulfobetaine |
|---|---|---|---|---|---|---|---|
| PAM 212 | 3 | >100 | 60 | 6 | ND | 50 | 7.5 |
| U-937 | >100 | >100 | >100 | 8 | >100 | 23 | 6 |
| HeLa | 68 | >100 | 75 | ND | 39 | 16 | 2.2 |
| C3H 10T1/2 | 6.5 | >100 | >100 | 53 | >100 | 54 | 3.3 |
| HL-60 | 9.3 | >100 | 11 | 0.5 | 37 | 8 | 1.6 |
| NIH 3T3 | >100 | >100 | >100 | 24 | >100 | 60 | 40 |
| K-562 | >100 | >100 | >100 | 5.5 | 19 | 32 | 15 |

TABLE 1-continued

Effect of Surfactants on Cell Growth
$IC_{50}$
(uM CONC. INHIBITING GROWTH OF THE CELLS BY 50%)

|  | (12-3S) $C_{12}$propyl-sulfobetaine | (8-3S) $C_8$propyl-sulfobetaine | (12-5B) $C_{12}$pentyl-betaine | (16-5B) $C_{16}$pentyl-betaine | (12-1B) $C_{12}$betaine | (16-1B) $C_{16}$betaine | (16-3S) $C_{16}$propyl sulfobetaine |
|---|---|---|---|---|---|---|---|
| B-16 | >100 | >100 | >100 | 20 | 90 | 52 | 54 |
| R6 | 45 | 78 | 78 | 18 | >100 | 45 | 14 |
| CPA-5 | 70 | >100 | >100 | 18 | >100 | 30 | 17 |
| cmc, uM | 2,200 | 200,000 | 5,100 | 10 | 2,400 | 14 | 28 |

Two of the compounds, 16-5B and 16-5S, were found to show considerable activity against all of the cell lines tested. The 16-1B compound was also effective against all of the cell lines, but in general, it was less active than 16-5S and 16-3S. For 16-5B, the $IC_{50}$'s (concentration of compound inhibiting growth by 50%) ranged over a 100-fold concentration range (from 0.5 to 53 uM). HL-60 cells were most sensitive to this compound ($IC_{50}$=0.5 uM) followed by K-562 cells, PAM 212 cells and U-937 cells ($IC_{50}$'s=5.5, 6 and 18 uM, respectively), and R6, CPA-5, B-16 and C3H 10T1/2 cells ($IC_{50}$'s=18, 18, 20, 24 and 53 uM, respectively). The variations in sensitivity of the cells to 16-5B indicates that there is selectivity in its action. Thus, this compound will selectively inhibit the growth of HL-60 leukemia cells over the other cell types. This selectivity is important since the cancer chemotherapy is dependent on the selective killing of tumor cells. 16-5B was also more growth inhibitory towards the two other leukemia cell lines tested (K-562 and U-937) although approximately ten times higher concentrations of the compound were required to inhibit cell growth. The compound was least effective against the fibroblast cell lines (C3H 10T1/2 and NIH 3T3) and in the melanoma cell line.

In general, each of the cell lines was found to be sensitive to 16-5S. HL-60, HeLa and C3H 10T1/2 cells were found to be most sensitive to the compound ($IC_{50}$'s=1.6, 2.2 and 3.3 uM, respectively), followed by U-937, PAM 212, R6, K562 and CPA-5 cells ($IC_{50}$'s=6, 7.5, 14, 15 and 17 uM, respectively). The least sensitive cell lines to 16-3S were NIH 3T3 ($IC_{50}$=40 uM) and B-16 cells ($IC_{50}$=54 uM). Except for C3H 10T1/2 cells, the $IC_{50}$'s with 16-5B and 16-3S were generally similar in each of the cell lines tested.

When compared to 16-5B and 16-3S, the cell lines were found to be generally less sensitive to compound 16-1B. The cell line most sensitive to the 16-1B was HL-60 cells ($IC_{50}$=8 uM) followed by HeLa (16 uM), U-937 (23 uM), CPA-5 (30 uM), K-562 (32 uM), R6 (45 uM), PAM 212 (50 uM), B-16 (52 uM), C3H 10T1/2 (54 uM) and NIH 3T3 cells (60 uM).

With each of the other compounds tested, growth in some of the cell lines was not inhibited. The least effective compound was the 8-3S. A low amount of activity was observed in R6 cells ($IC_{50}$=78 uM) while no activity was observed in any of the other cell types ($IC_{50}$>100 uM). A greater amount of activity was observed with compound 12-5B. A strong response was observed in HL-60 cells ($IC_{50}$=11 uM). Weaker activity was observed in PAM 212 ($IC_{50}$=60 uM), HeLa (75 uM) and R6 cells (78 uM). No activity was observed in U-937, C3H 10T1/2, NIH 3T3, K562, B-16 and CPA-5 cells ($IC_{50}$>100 uM).

PAM 212 cells were most sensitive to compound 12-3S ($IC_{50}$=3 uM) followed by C3H 10T1/2 ($IC_{50}$=6.5 uM) and HL-60 cells ($IC_{50}$=9.3 uM). Weaker activity was observed in R6 cells ($IC_{50}$=45 uM), HeLa (58 uM) and CPA-5 cells (70 uM). No activity was observed in U-937, NIH 3T3, K-562 and B-16 cells ($IC_{50}$>100 uM).

In contrast, K562 cells were most sensitive to compound 12-1B ($IC_{50}$=19 uM) followed by HL-60 ($IC_{50}$=37 uM) and HeLa cells ($IC_{50}$=39 uM). Little or no activity was observed in B-16 ($IC_{50}$=90 uM), U-937, C3H 10T1/2, NIH 3T3, R6 and CPA-5 cells ($IC_{50}$'s>100 uM).

Figure 1A:
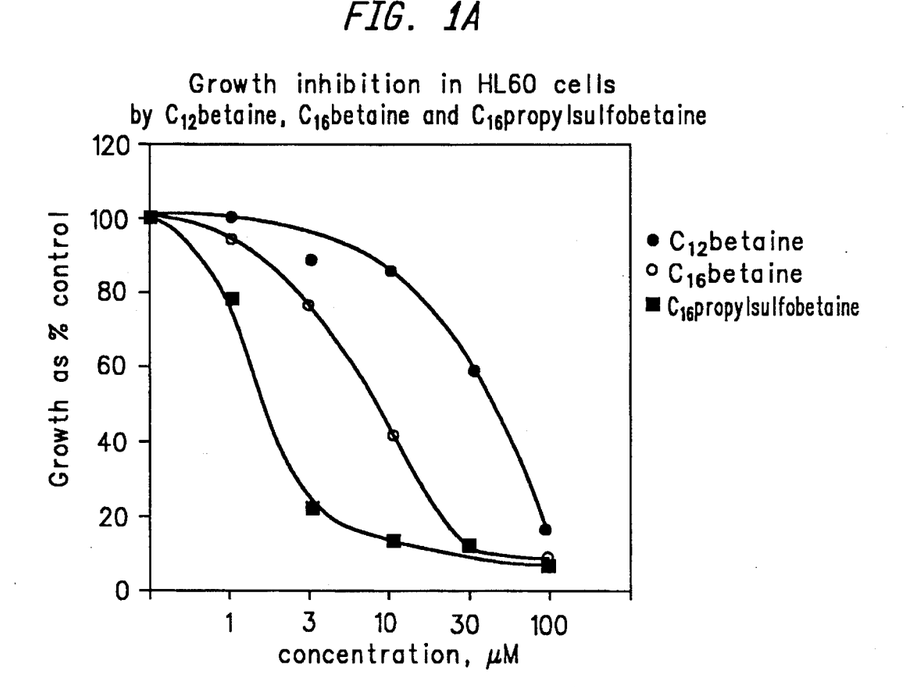
FIGS. 1A and 1B illustrate the ability of representative betaine and sulfobetaines of the invention to inhibit the growth of HL-60 cells in culture. Each data point is the average of duplicate samples.
Figure 1B:
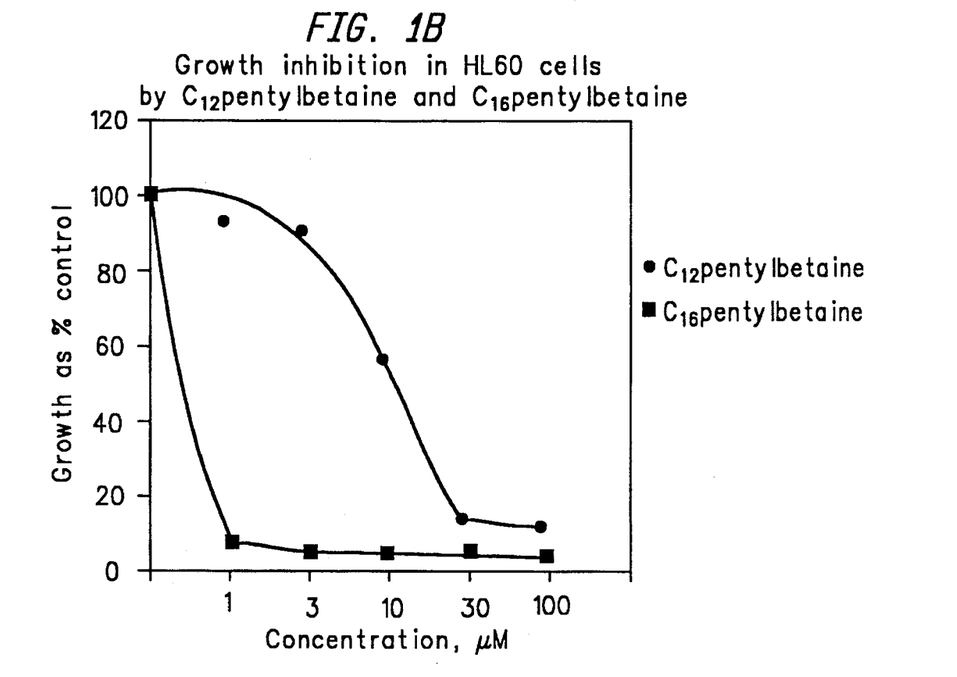

Based on this data it is clear that there are certain structure activity relationships for the cell lines. Thus, as shown in FIG. 1, for the most sensitive cell line (HL-60), the activity of 16-5B>16-3S>16-1B>12-3S>12-5B>12-1B>8-3S. For HeLa cells, 16-3S>16-1B>12-1B>12-3S>12-5B>8-3S. In contrast, PAM 212 cells were most sensitive to 12-3S followed by 16-5B and 16-3S. Each of the other cell lines (except for C3H 10T1/2 and U-937 cells) were most sensitive to 16-5B. The reasons for differences in sensitivity among the cell lines is not clear and may be related to unique characteristics of cells derived from different tissues. Among the leukemia cells, only HL-60 was found to be sensitive to 12-3S and 12-5B. They were also 10 to 100-fold more sensitive to 16-5B. Thus, the sensitivity of the leukemias to individual surfactants may also depend on the cellular origin of the tumor.

Example 3

Assays for DNA, RNA and Protein Synthesis

The 16-5B compound was evaluated further using HeLa cells to gain some insight into the mechanism of action of this group of compounds. In these studies, the ability of this compound to inhibit macromolecular synthesis in the cells was examined. The effects of 16-5B on DNA, RNA and protein synthesis was monitored using labeled thymidine, uridine or leucine, respectively. These precursors readily incorporate into the appropriate cellular macromolecules in the cells.

For assays of macromolecular biosynthesis in HeLa cells, cells were seeded into 60 mm culture dishes (Falcon Labware, Lincoln Park, N.J.) at a density $1 \times 10^5$/ml in 5 mls of cell culture medium. Cells were allowed to grow at 37° C. for 48 hours before use. Culture plates were then removed from the incubator and washed with phosphate buffered saline. The cells were then incubated with increasing concentrations of the 16-5B in 2 ml of serum-free Dulbecco's modified Eagle's medium supplemented with 0.075% sodium bicarbonate. Control cultures were incubated in cell culture medium without surfactant. After 30 minutes, $^3$H-thymidine ($5 \times 10^5$ cpm/ml, specific activity 10 Ci/mmol, ICN Radiochemicals, Irvine, Calif.), $^3$H-leucine ($5 \times 10^5$ cpm/ml, specific activity 108 Ci/mmol, ICN Radiochemicals) or $^3$H-uridine (5×10$^5$ cpm/ml, specific activity 37 Ci/mmol, ICN Radiochemicals) were added directly to the culture medium to measure DNA, protein and RNA synthesis, respectively. Cells were then incubated at 37° C. for 1 hour with $^3$H-thymidine, 2 hours with $^3$H-uridine or 4 hours with $^3$H-leucine. Radioactive medium was then removed from the culture plates and the cells were washed 5 times with 2 ml of ice cold phosphate buffered saline. Three ml of ice cold 5% trichloroacetic acid was then added to each plate. After 10 minutes the trichloroacetic acid was drained from the plates and the cells washed 5 times with an additional 5 ml of ice cold 5% trichloroacetic acid. The remaining acid insoluble cellular material was solubilized with 2 ml of 0.2N sodium hydroxide. Two 0.5 ml aliquots were neutralized and counted for radioactivity using a scintillation counter.

Figure 2A:
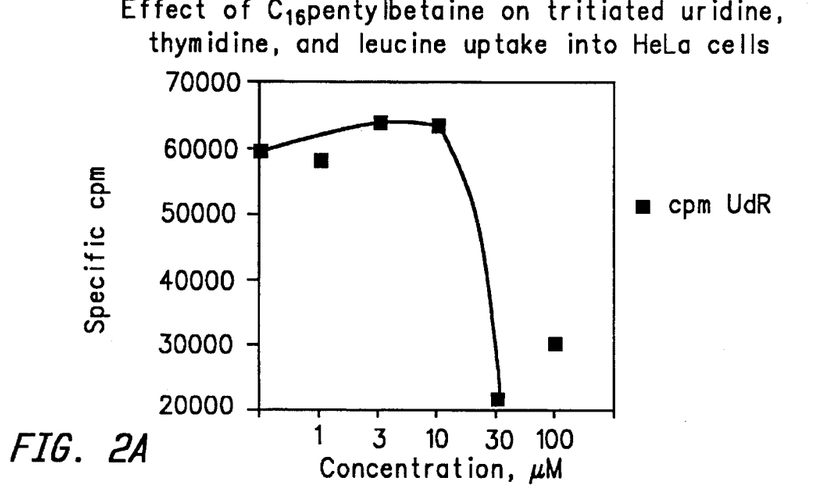
FIGS. 2A–2C provide three graphs illustrating the effectiveness of the $C_{16}$pentylbetaine in causing a concentration-dependent inhibition of DNA, RNA and protein synthesis in HeLa cells as monitored using labeled thymidine, uridine or leucine, respectively.
Figure 2B:
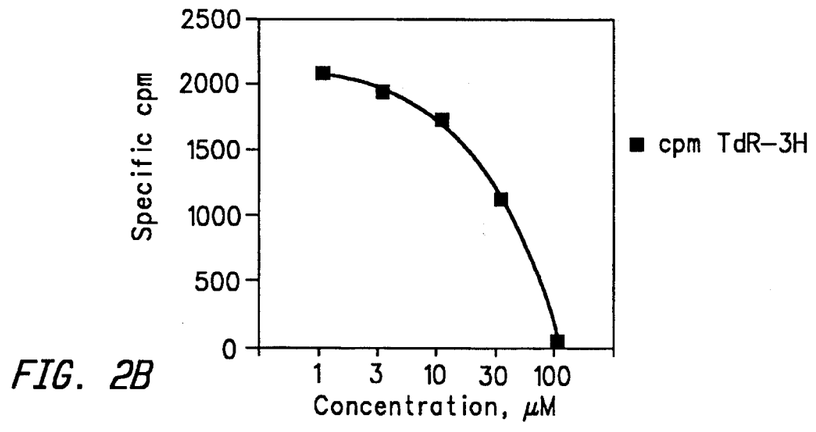
Figure 2C:
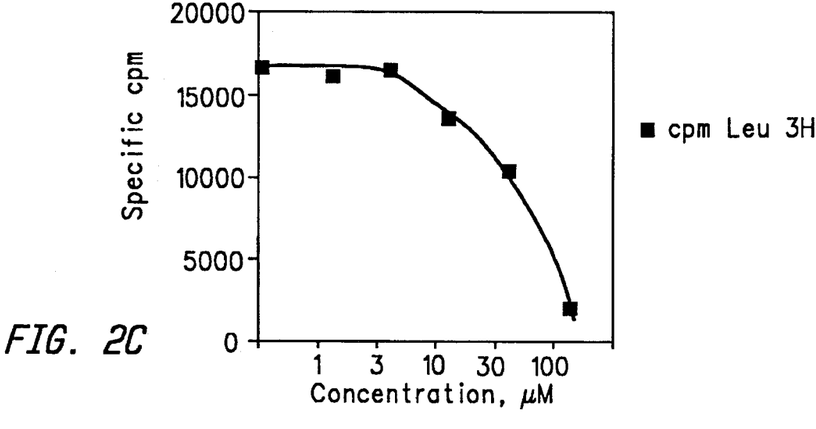

The 16-5B compound caused a concentration-dependent inhibition of DNA, RNA and protein biosynthesis in the cells. For each process, the compound was effective in the uM concentration range. As shown in FIG. 2, a similar IC$_{50}$ (30 uM) for thymidine, uridine and leucine uptake into the cells was observed.

Based on this data it is concluded that 16-5B is an inhibitor of macromolecular biosynthesis in HeLa cells. However, since the same concentration was effective in inhibiting DNA, RNA and protein synthesis, the compound does not appear to selectively inhibit any of these processes. Since the surfactants are known to be membrane active, it is possible that this compound is more selective towards cellular membranes and this might be its site of action.

Example 4

Inhibition of Endothelial Cell Growth

Figure 3A:
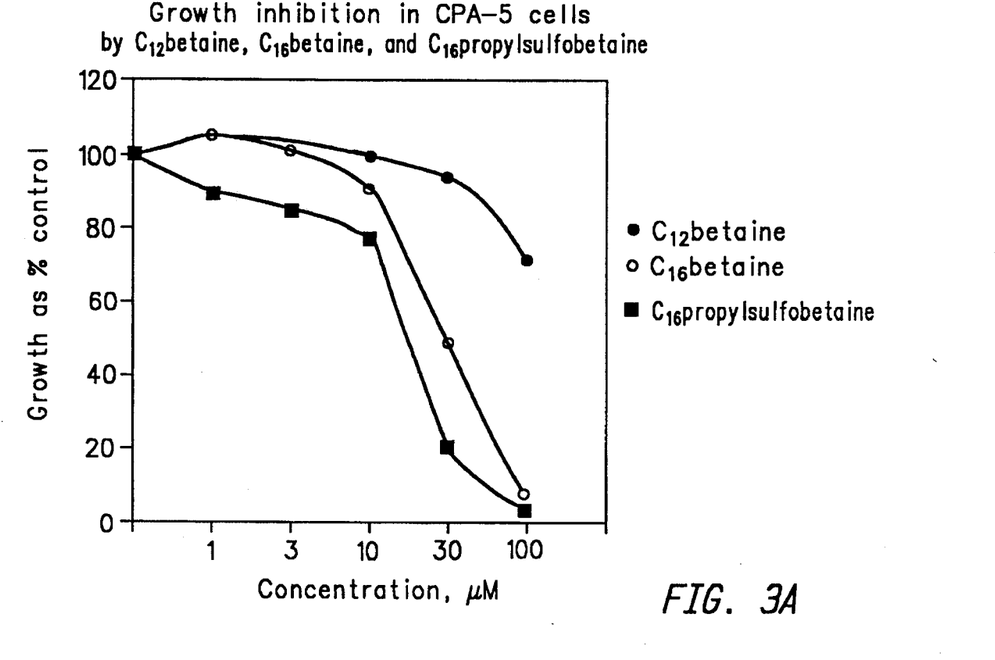
FIGS. 3A and 3B provide two graphs illustrating the activity of certain betaines and sulfobetaines in inhibiting the growth of a bovine aortic endothelial cell line, CPA-5, a non-tumorous cell line.
Figure 3B:
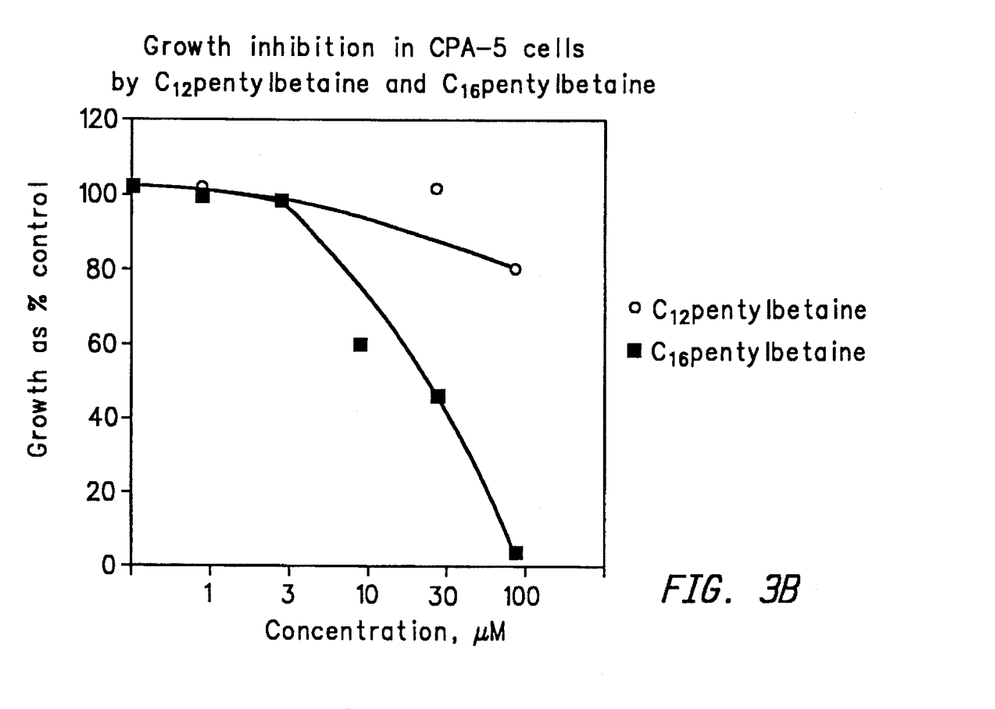

The compounds were tested as inhibitors of growth in the bovine aortic endothelial cell line CPA-5 as taught in Example 2 in order to evaluate the possibility that they may be anti-angiogenesis agents. A hallmark of angiogenesis is the outgrowth of endothelial cells which are required in the formation of new blood vessels. This process is a critical factor in the vascularization of tumors. Inhibition of neovascularization limits the growth of tumors and would be an effective means of treating cancer. FIG. 3 illustrates that three of the compounds, 8-3S, 12-5B and 12-1B, had no activity against the CPA-5 cell line in the concentration range tested (IC$_{50}$=>100 uM), while only relatively high concentrations of 12-3S (IC$_{50}$=70 uM) were effective in inhibiting the growth of CPA-5 cells. As indicated above, with several exceptions, these compounds were also not very effective in inhibiting the growth of each of the other cell types. In contrast, compounds 16-3S, 16-5B and 16-1B (IC$_{50}$'s=17, 18 and 30 uM, respectively) demonstrated some activity in inhibiting growth of the CPA-5 cells (FIG. 3). These data indicate that the three compounds exhibit anti-angiogenic properties and may be evaluated further as antitumor agents.

Although the invention has been described with references to the presently preferred embodiments, it should be understood that various modifications can be made by those skilled in the art without departing from the invention. Accordingly, the invention is limited only by the following claims.

We claim:

1. A method for inhibiting the growth of melanoma, leukemia or adenocarcinoma cells which comprises administering to melanoma, leukemia or adenocarcinoma cell hosts a pharmaceutical composition containing an effective cellular growth inhibiting amount of a quaternary ammonium betaine of the formula:

wherein

R$_1$ is independently selected from the group consisting of lower alkyls and lower alkylaryls;

X is a carboxyl anion;

m is an integer from 11 to 15 inclusive; and n is an integer from 1 to 5 inclusive; provided that the combination of X, m and n result in a compound having a Krafft point at or below 25° C. and a critical micelle concentration about or less than 50 uM.

2. The method of claim 1 wherein said proliferating cells are in culture.

3. The method of claim 1 wherein each R$_1$ is methyl.

4. The method of claim 1 wherein m is 11.

5. The method of claim 1 wherein m is 15.

6. The method of claim 1 wherein n is 1.

7. The method of claim 1 wherein n is 5.

8. The method of claim 1, wherein the compound is:

9. The method of claim 1, wherein the compound is:

10. The method of claim 1, wherein the cell hosts are melanoma cells.

11. The method of claim 10, wherein said compound has the structure:

where m is 11 or 15, and n is 1 or 5.

12. The method of claim 1, wherein the cell hosts are leukemia cells.

13. The method of claim 12, wherein said compound has the structure:

where m is 11 or 15, and n is 1 or 5.

14. The method of claim 1, wherein the cell hosts are adenocarcinoma cells.

15. The method of claim 14, wherein said compound has the structure:

where m is 11 or 15, and n is 1 or 5.

16. A method for treating melanomas, leukemias or adenocarcinomas which comprises administering to proliferating melanoma, leukemia or adenocarcinoma cell hosts a pharmaceutical composition containing an antineoplasia effective amount of the compound:

wherein

X is a carboxyl anion; and n is an integer from 1 to 5 inclusive; provided that the combination of X, m and n result in a compound having a Krafft point at or below 25° C. and a critical micelle concentration about or less than 50 uM.

17. The method of claim 16 wherein n is 1.

18. The method of claim 16 wherein n is 3.

19. The method of claim 16 wherein n is 5.

20. The method according to claim 16 wherein the compound is:

21. The method according to claim 16 wherein the compound is:

22. The method of claim 16, wherein the compound is:

* * * * *